United States Patent
Ferguson

(10) Patent No.: US 8,546,733 B2
(45) Date of Patent: *Oct. 1, 2013

(54) METHOD OF MANUFACTURING A SHAPED COMPONENT

(75) Inventor: Patrick Ferguson, North Shields (GB)

(73) Assignee: NEL Technologies Limited, Northumberland (GB)

( * ) Notice: Subject to any disclaimer, the term of this patent is extended or adjusted under 35 U.S.C. 154(b) by 233 days.

This patent is subject to a terminal disclaimer.

(21) Appl. No.: 12/828,440

(22) Filed: Jul. 1, 2010

(65) Prior Publication Data
US 2010/0308490 A1     Dec. 9, 2010

Related U.S. Application Data

(62) Division of application No. 10/559,023, filed on Feb. 12, 2007, now Pat. No. 7,767,939.

(30) Foreign Application Priority Data

Jun. 2, 2003    (GB) .................................. 0312553.1

(51) Int. Cl.
*H05B 3/34* (2006.01)

(52) U.S. Cl.
USPC ............ 219/549; 219/528; 219/544; 219/545

(58) Field of Classification Search
USPC ................. 219/219, 549, 209, 211, 216, 528, 219/529, 548, 544–545
See application file for complete search history.

(56) References Cited

U.S. PATENT DOCUMENTS

| | | |
|---|---|---|
| 2,717,949 A | 9/1955 | Challenner |
| 3,296,415 A | 1/1967 | Eisler |
| 3,660,088 A | 5/1972 | Lungsager |
| 3,767,398 A | 10/1973 | Morgan |

(Continued)

FOREIGN PATENT DOCUMENTS

| | | |
|---|---|---|
| DE | 3210097 | 9/1983 |
| GB | 2092868 A | 8/1982 |

(Continued)

OTHER PUBLICATIONS

Adeyeye, C. M. and Price, J.C., "Development and Evaluation of Sustained Release Ibuprofen-Wax Microspheres: I. Effect of Formulation Variables on Physical Characteristics", Pharmaceutical Research, vol. 8, No. 11, pp. 1377-1383 (1991).

(Continued)

*Primary Examiner* — Henry Yuen
*Assistant Examiner* — James Sims, III
(74) *Attorney, Agent, or Firm* — Barlow, Josephs & Holmes, Ltd.

(57) ABSTRACT

A heater element for formed components is disclosed, along with the final formed component itself. The heater element is produced by photochemically etching a suitable heater track pattern from porous metallized fabric such a nickel coated woven polyester. The heater element is located within a mold. Thermo-formable material is then applied to the mold and the final component is shaped according to the shape of the mold. The final component has a heater element located within it. The component may have microencapsulated agents for initiation by operation of the heater element. Furthermore, the final component may have one or more digital images printed onto the surface for the purposes of decoration or personalization.

8 Claims, 7 Drawing Sheets

(56) References Cited

U.S. PATENT DOCUMENTS

| | | | |
|---|---|---|---|
| 4,066,078 A | 1/1978 | Berg | |
| 4,201,825 A | 5/1980 | Ebneth | |
| 4,257,176 A | 3/1981 | Hartung et al. | |
| 4,508,776 A | 4/1985 | Smith | |
| 4,565,745 A | 1/1986 | Kaminskas | |
| 4,743,740 A | 5/1988 | Adee | |
| 4,764,665 A | 8/1988 | Orban et al. | |
| 4,798,933 A | 1/1989 | Annovi | |
| 4,948,951 A | 8/1990 | Balzano | |
| 5,041,717 A | 8/1991 | Shay, III et al. | |
| 5,352,862 A | 10/1994 | Barr | |
| 5,534,021 A | 7/1996 | Dvoretzky et al. | |
| 5,552,371 A * | 9/1996 | Chen et al. | 505/160 |
| 5,580,573 A * | 12/1996 | Kydonieus et al. | 424/449 |
| 5,648,003 A | 7/1997 | Liang et al. | |
| 5,829,171 A | 11/1998 | Weber et al. | |
| 5,925,275 A * | 7/1999 | Lawson et al. | 219/543 |
| 5,932,496 A | 8/1999 | Morris et al. | |
| 6,172,344 B1 | 1/2001 | Gordon et al. | |
| 6,227,458 B1 | 5/2001 | Dever et al. | |
| 6,229,123 B1 | 5/2001 | Kochman et al. | |
| 6,294,313 B1 | 9/2001 | Kobayashi et al. | |
| 6,309,986 B1 | 10/2001 | Flashinski et al. | |
| 6,423,018 B1 | 7/2002 | Augustine | |
| 6,436,063 B1 | 8/2002 | Augustine et al. | |
| 6,501,055 B2 | 12/2002 | Rock et al. | |
| 6,551,560 B1 | 4/2003 | Flashinski et al. | |
| 6,613,350 B1 | 9/2003 | Zhang et al. | |
| 7,115,844 B2 | 10/2006 | Ferguson | |
| 2001/0002669 A1 | 6/2001 | Kochman et al. | |
| 2002/0131062 A1 * | 9/2002 | Neri et al. | 358/1.9 |
| 2003/0124167 A1 | 7/2003 | Thies | |
| 2004/0155029 A1 * | 8/2004 | Haag | 219/543 |
| 2007/0187392 A1 | 8/2007 | Ferguson | |
| 2007/0210051 A1 | 9/2007 | Ferguson | |

FOREIGN PATENT DOCUMENTS

| | | |
|---|---|---|
| GB | 2175849 A | 12/1986 |
| GB | 2205496 A | 12/1988 |
| GB | 2336514 A | 10/1999 |
| GB | 2383197 A | 6/2003 |
| JP | 6147686 | 3/1986 |
| JP | 03037021 | 2/1991 |
| JP | 04002079 | 1/1992 |
| WO | 8810058 A1 | 12/1988 |
| WO | 0101855 A1 | 1/2001 |
| WO | 0124580 A1 | 5/2001 |
| WO | 03039417 A2 | 5/2003 |
| WO | 03053101 A1 | 6/2003 |

OTHER PUBLICATIONS

Adeyeye, C. M. and Price, J.C., "Development and Evaluation of Sustained Release Ibuprofen-Wax Microspheres: II. In vitro Dissolution Studies" Pharmaceutical Research vol. 11, No. 4, pp. 575-579 (1994).

Adeyeye, C. M. and Price, J.C. "Chemical, dissolution stability and microscopic evaluation of suspensions of Ibuprofen-wax microspheres", Journal of Microencapsulation, vol. 14, pp. 357-377 (1997).

Woodhead Publishing Series in Textiles: No. 90, "Smart Textile coatings and laminates", 2010.

US 6,290,977, 09/2001, Friars et al. (withdrawn)

* cited by examiner

Fig. 5A
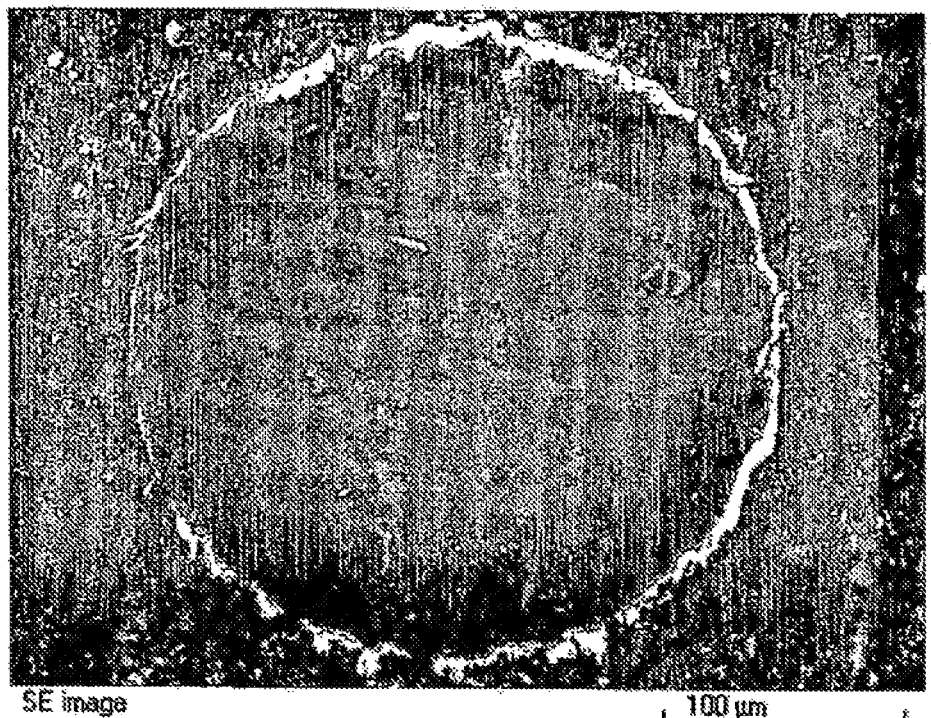
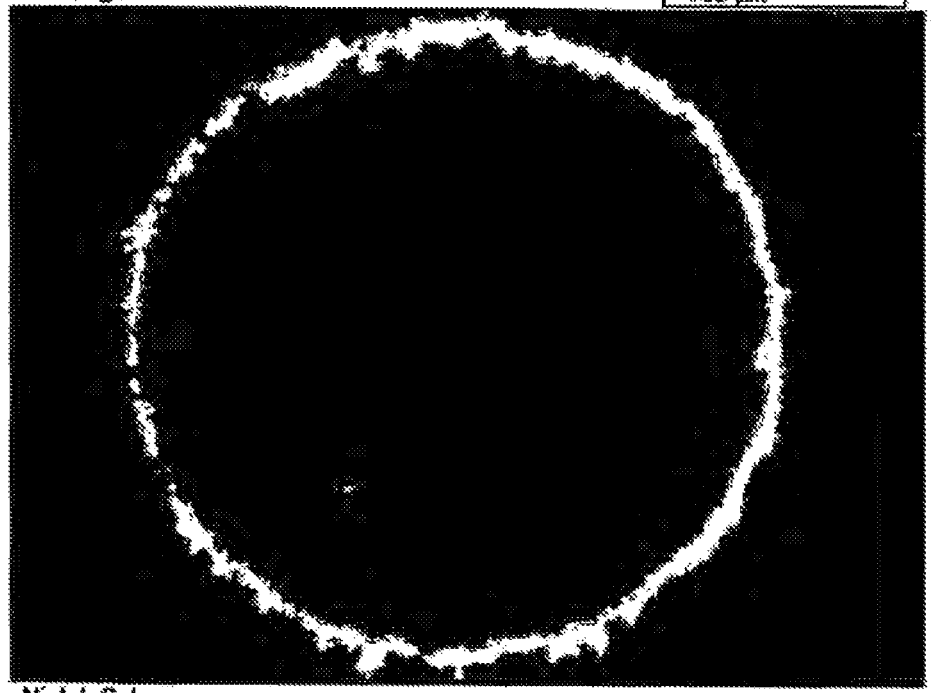
Fig. 5B

METHOD OF MANUFACTURING A SHAPED COMPONENT

CROSS REFERENCE TO RELATED APPLICATION

This application is a divisional continuation application of application Ser. No. 10/559,023, filed Feb. 12, 2007, now U.S. Pat. No. 7,767,939 the entire contents thereof is incorporated herein by reference.

BACKGROUND TO THE INVENTION

1. Field of the Invention

The invention relates to a formed component heater element. In a preferred embodiment it relates to a porous flexible heater and associated functional chemical delivery system for incorporation into formed components.

2. Related Art

The designs of various active heating systems, capable of evolving heat in response to an energy input are known. These systems incorporate electrically conductive materials in sheets, wires or filaments as heating elements. Such elements generate heat when carrying an electrical current. The ability to incorporate such elements into products varies greatly depending on the element type and the typically operating temperature of the element in use. In the case of heating products made using forming techniques such as casting, calendaring, pressing or compression, extrusion and injection moulding, the heating elements used are typically trace elements which comprise insulated conductive wires, yarns and filaments. Examples of such products include undertile heaters used in flooring applications and toilet seat heaters.

SUMMARY OF THE INVENTION

The present inventor has realised that there is a need for a versatile, low cost, flexible heater which is capable of reliably being incorporated into formed components made from polymeric and other formable materials.

Accordingly, in a first aspect, the present invention provides a formed component heater element formed from flexible metallised fabric.

Preferably, the heater element is porous.

The heater element can be utilised in numerous product applications. Suitable product applications include, for example, wall tiles, plasterboard, floor tiles, toilet seats, insect repellent traps, air fresheners etc.

Preferably, the heater element is formed by etching (e.g. photochemical etching) of metallised mesh. Subsequently, the heater element may be incorporated as an integral part of the formed component during the product manufacturing process.

Details of the construction, manufacture and heating performance of a suitable flexible, porous etched metallised fabric heater are described in WO03/053101, the content of which is incorporated by reference in its entirety. WO03/053101 claims priority from UK Patent Application No. 0228999.9, filed 14 Dec. 2001.

Conveniently, the metal coating is nickel, although any suitable resistive metal can be used. The mesh may have one of various weave types. The threads of the mesh may have various diameters up to 1000 microns. The thread counts may be between 5 and 1500 per cm. The metal coating may be of various weights per square meter which can be applied to the mesh by various coating techniques.

The material used in mesh production can be any suitable material which has a softening point in excess of the temperature of that used in the end product manufacturing process, and the desired operating temperature of the heater in the formed product.

The open porous nature of the heater element allows the flow of materials during the end product manufacturing process. This allows the substantial elimination of trapped air to provide intimate contact with the materials used in the product.

The heater is typically connectable by the use of a suitable connector to a battery or mains voltage supply and can deliver significant thermal energy to the component.

The width, length and shape of the etched heater track can be selected during manufacture from a wide range so as to optimise the heater element performance or to provide differential heating.

Preferably, the heater element has termination pads. These are at the end of the etched track and allow connection of the heater element to a power supply/control system, which may be stored in the formed component or elsewhere.

The termination pads for the track or tracks may be formed on the fabric at an elongate flexible tail portion of the fabric. In this way, the heat-generating tracks may be connected to a suitable power supply via the termination pads at the tail portion. This avoids the need for conventional wires to be trailed through the formed component from the power supply to the fabric heater embedded in the formed component.

Preferably, the heater element is capable of being controlled to regulate the rate of heating and/or its maximum heat output. Regulation can be achieved either manually via a suitable control device e.g. incorporating a surface mounted thermistor or automatically by limiting the resistance of the heater itself.

If required, differential heating can be achieved in the formed component by appropriate adjustment of the heater element geometry.

The heater element is intended to be incorporated into formed components by the component manufacturer without the need for major modifications to the construction and design of existing equipment.

In another aspect of the invention, there is provided a formed component having incorporated in it a heater element according to the first aspect of the invention.

The present inventor has realised that the present invention may have a further advantage over known formed components. It is preferred to incorporate functional chemicals or agents into a formed component according to an embodiment of the invention, said functional chemicals being ones that are capable of being initiated by operation of the heater element.

Preferably, the invention provides a formed component as set out above having heat-activatable agents for release due to heat generated by the heater element.

The chemicals (or agents) of interest include antimicrobials (for suppressing or killing microbiological activity, e.g. bacteria), insect repellants (for repelling insects such as mosquitoes etc.), fragrances and perfumes.

In a preferred approach, the chemicals (or agents) of interest are microencapsulated in microcapsules. Suitable microcapsules are those that melt at a particular initiation temperature. Alternative microcapsules are those that allow diffusion of the active chemicals through their walls to effect a slow release mechanism from the formed component. By appropriate temperature control, the heater element may then be used to initiate the delivery of such active chemicals or agents.

It will be understood that by the encapsulation of various active chemicals and the use of microcapsules having different thermal characteristics, the timing of the delivery of each chemical can be controlled as required. Normally, the microencapsulated components will not form part of the heater element itself. Instead they will typically be contained within other parts of the formed component. The release of the chemicals is typically achieved using the heater, which is preferably adjacent the part containing the microencapsulated components.

When the material used for the formed component is a compatible polymer (e.g. polyamide, polyester or blends thereof), the formed component may be Thermostatic Printed (Registered Trade Mark) or dye sublimation printed in order to improve its aesthetic design and appearance for the purpose of personalisation. Ink jet printing can also be used for the same purpose. The high resolution digital imaging printing processes typically do not interfere with the performance of the heater unit.

BRIEF DESCRIPTION OF THE DRAWINGS

Preferred embodiments of the present invention are set out below by way of example, with reference to the accompanying drawings, in which:

FIG. 5A shows an enlarged SEM secondary electron image of a part of the image shown in FIG. 4.

FIG. 5B shows an image corresponding to that of FIG. 5, but taken using elemental analysis (EDX) for nickel.

DESCRIPTION OF THE PREFERRED EMBODIMENTS

Figure 1:
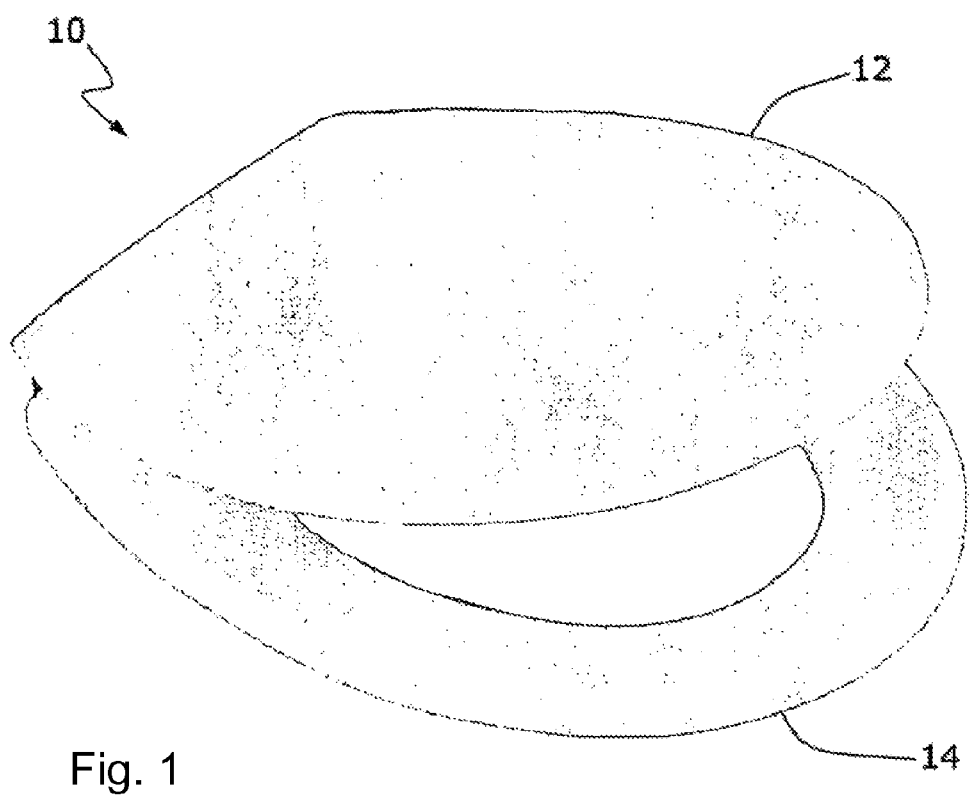
FIG. 1 shows a schematic perspective view of a moulded toilet seat and lid. The toilet seat is according to an embodiment of the invention.
Figure 7A:
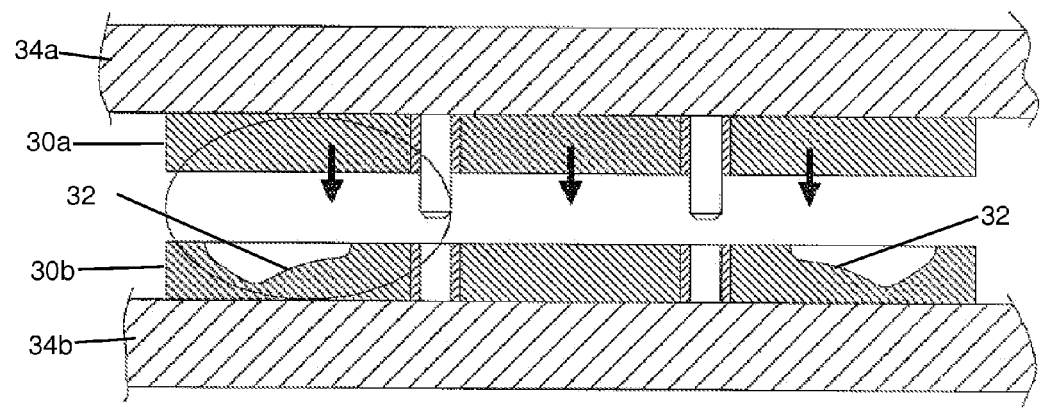
FIG. 7A shows a cross-sectional view of a compression moulding press and an empty toilet seat mould tool mounted therein with the upper press being movable in the direction of the arrows and the lower press being fixed.
Figure 7B:
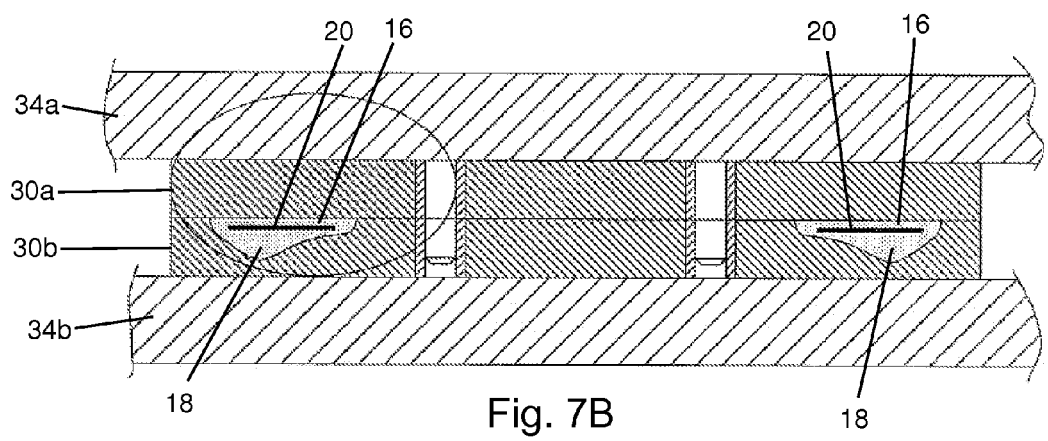
FIG. 7B shows a cross-sectional view of the compression moulding press and mould tool of FIG. 7A after the moulding operation.
Figure 8A:
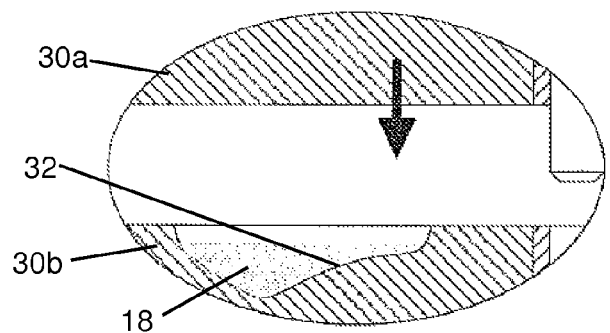
FIGS. 8A-D show the sequence of loading the urea formaldehyde granules and heater element in the mould tool and the formation of the moulded part when the mould tool closes.
Figure 8B:
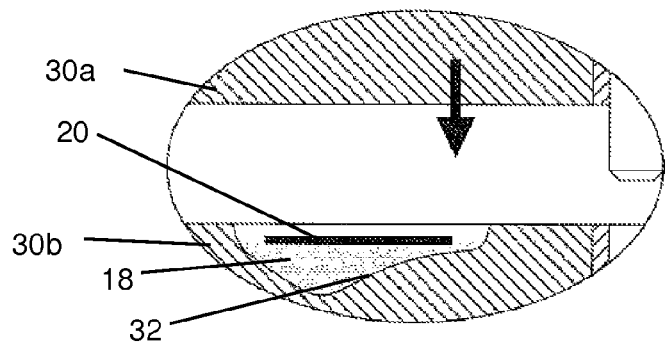
Figure 8C:
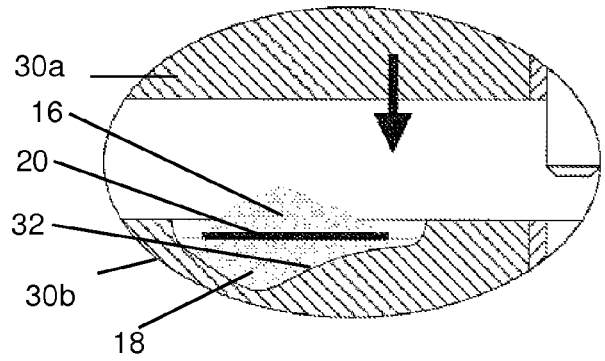
Figure 8D:
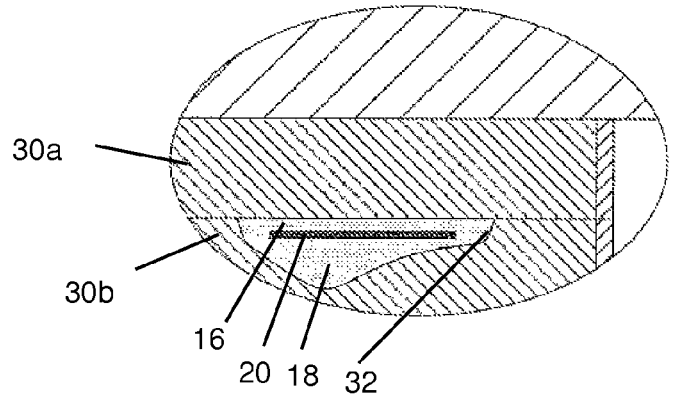

FIG. 1 shows a combination 10 of a toilet seat 14 attached via a hinge (not shown) to a toilet lid 12. Both the toilet seat 14 and the lid 12 are formed by compression moulding of urea formaldehyde (a thermoset polymeric material), moulding of the toilet seat being seen in FIGS. 7A and 7B. Particularly preferred materials for compression moulding include urea formaldehyde, urea formaldehyde resin, melamine formaldehyde and polypropylene. In alternative embodiments, these components are formed by injection moulding from thermoplastic materials.

Figure 2:
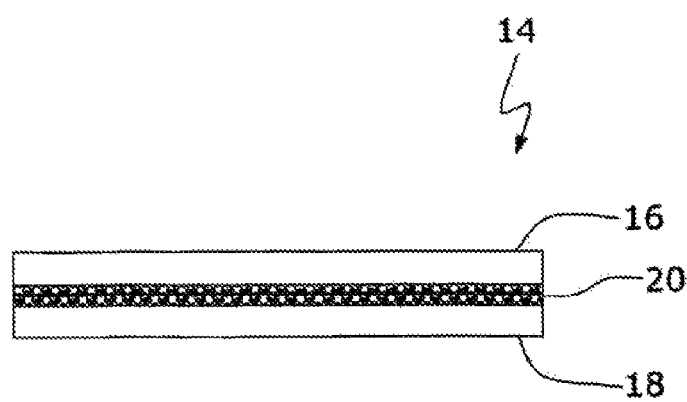
FIG. 2 shows a schematic cross-sectional view of part of a moulded toilet seat according to an embodiment of the invention.
Figure 9A:
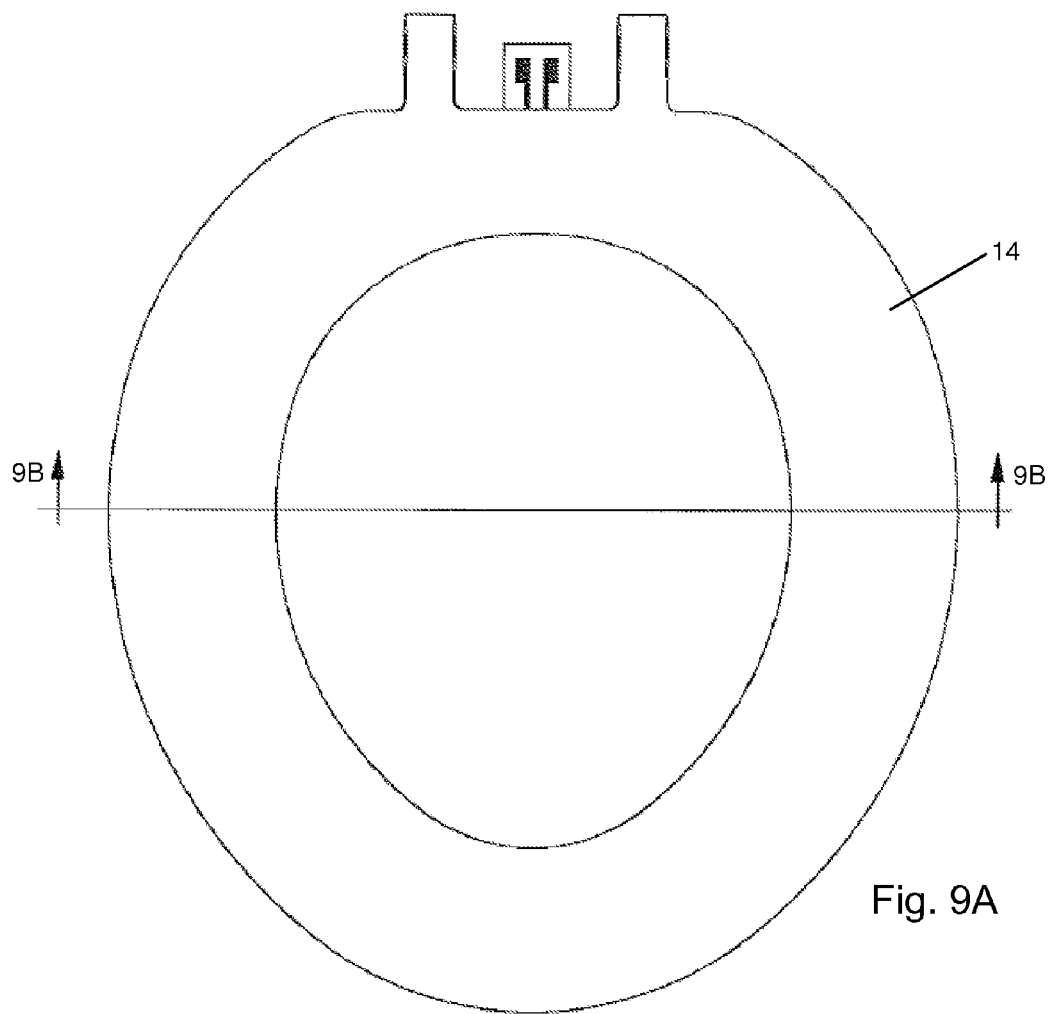
FIG. 9A shows a top view of the completed moulded toilet seat containing the heater element.
Figure 9B:
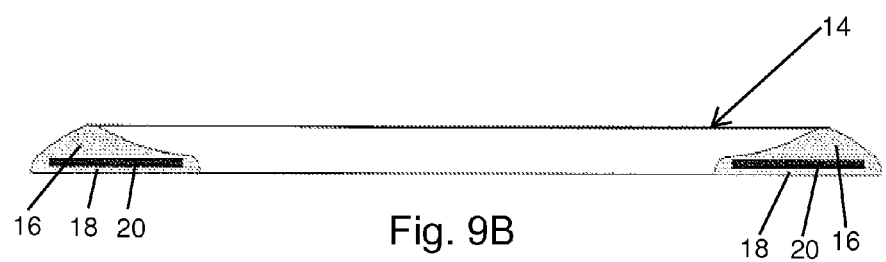
FIG. 9B is a cross-sectional view through the line 9B-9B of FIG. 9A.

The toilet seat 14 has a heater element 20 located within it. Part of the toilet seat 14 is shown in schematic cross-section in FIG. 2. Upper layer 16 and lower layer 18 of compression moulded thermoset urea formaldehyde retain the heater element mesh 20 in position, as in FIG. 7B. To form the toilet seat, the heater element 20 is located in a cavity 32 of a suitable mould 30a, 30b mounted in a press 34a, 34b and the material of layers 16 and 18 is compression moulded around the heater element 20. As seen in FIGS. 8A through 8D, the porous nature of the heater element 20 allows the material of layers 16, 18 to flow into the open pores of the heater, eliminating air bubbles in the heater element and ensuring good thermal contact between the heater element and the material of the layers 16, 18. In this way, the heater element is fully integrated into the toilet seat, as can be seen in FIGS. 9A and 9B.

Figure 3:
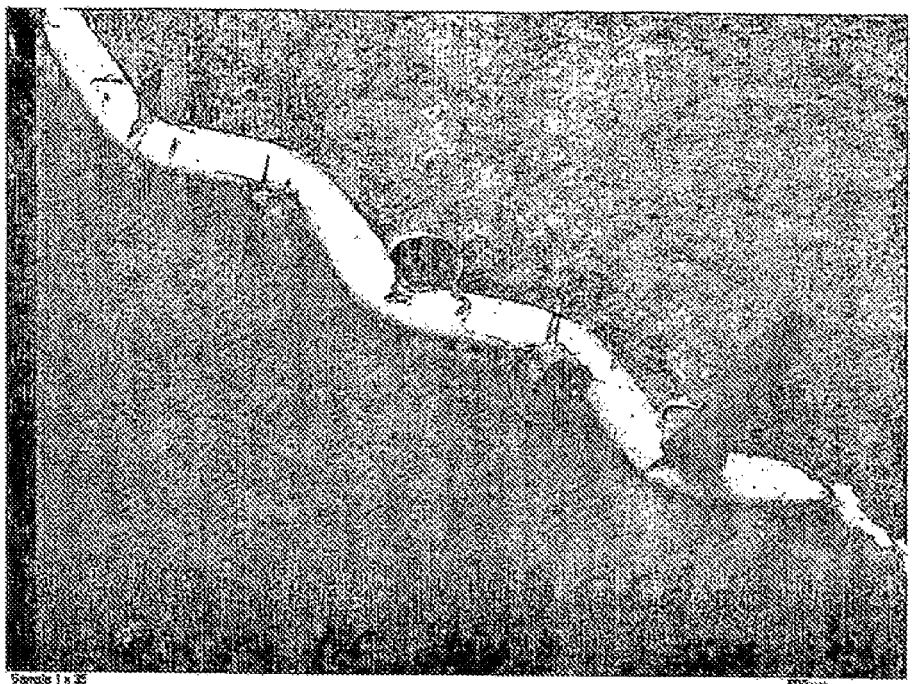
FIG. 3 shows a scanning electron microscopy image (SEM) of a fracture surface of a formed component according to an embodiment of the invention.

FIG. 3 shows an SEM image of a fracture surface of a heater element according to an embodiment of the invention embedded in compression moulded urea formaldehyde. The heater element is woven polyester coated with nickel. The part of the heater element shown in FIG. 3 protruding from the urea formaldehyde matrix is part of a conductive track. The continuous nickel coating on the threads is clearly visible. Other parts of the heater element (not shown) will have had their nickel coating etched away, as described below. The sample of FIG. 3 was fractured by freezing it in liquid nitrogen and performing a brittle fracture on the sample.

Figure 4:
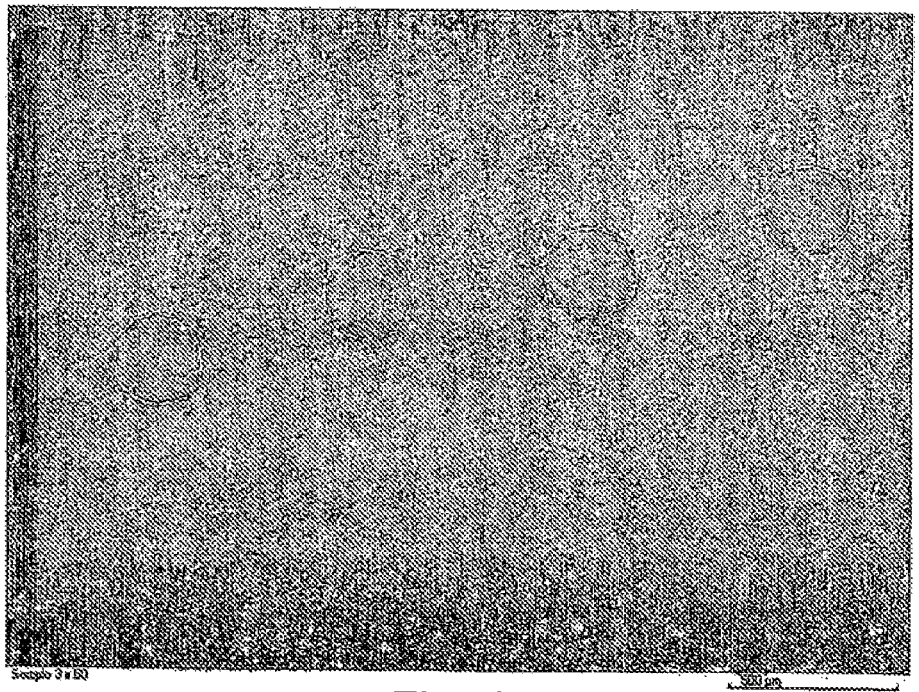
FIG. 4 shows a scanning electron microscopy image (SEM) of a polished cross-section of a formed component according to an embodiment of the invention.

FIG. 4 shows a similar sample to that of FIG. 3, but here the sample has been polished. Four threads of the heater element are shown in cross section, embedded in the urea formaldehyde matrix.

FIG. 5A shows a magnified view of the right hand thread shown in FIG. 4. FIG. 5A, like FIGS. 3 and 4, is a secondary electron SEM image.

FIG. 5B is an image corresponding to that of FIG. 5A, except that this image was taken using EDX analysis, in a known way. The bright areas on the image correspond to areas having a significant concentration of nickel. It is clear that the nickel coating of the threads (for those parts of the heater element that have not been etched) survives the compression moulding of the component, so that the heater element is operational even after the compression moulding.

The way in which the heater element 20 is formed will now be set out.

Heater element 20 is formed by taking a nickel coated polyester woven fabric and cutting it to the desired shape. A suitable material is the commercially available metallised fabric Metalester®, a woven electroless nickel plated polyester mesh. Such fabrics are available with a variety of thread thicknesses, thread spacings, type of weave and weight of nickel. Threads may typically have a diameter within the range 24 to 600 micrometers (microns), a thread count of between 4 and 737 per cm, and a metal coating of varying weight per square meter.

Suitable fabrics may be coated with a continuous layer of metal after manufacture, for example by sputtering, by chemical reduction or by electro-deposition, which results in total encapsulation of all the threads of the mesh in metal. In an alternative mesh, the individual warp and weft threads may be metallised prior to fabric production, for example by sputtering, by chemical reduction or by electro-deposition.

After selecting the desired metallised fabric and cutting it to the required shape, the desired track pattern is then photochemically etched from the fabric. This is done by first designing and generating a suitable phototool, in a way well known to the skilled person. Next, the fabric is mounted onto a hinged frame of brown styrene board, so that the otherwise flimsy fabric can be more readily handled. The fabric is then cleaned with a commercial surface cleaning agent to assist in the adhesion of the photoresist. Then, the photoresist is applied, typically by dip-coating the fabric into a liquid photoresist to ensure application of the photoresist to all parts of the fabric by immersion.

Figure 6A:
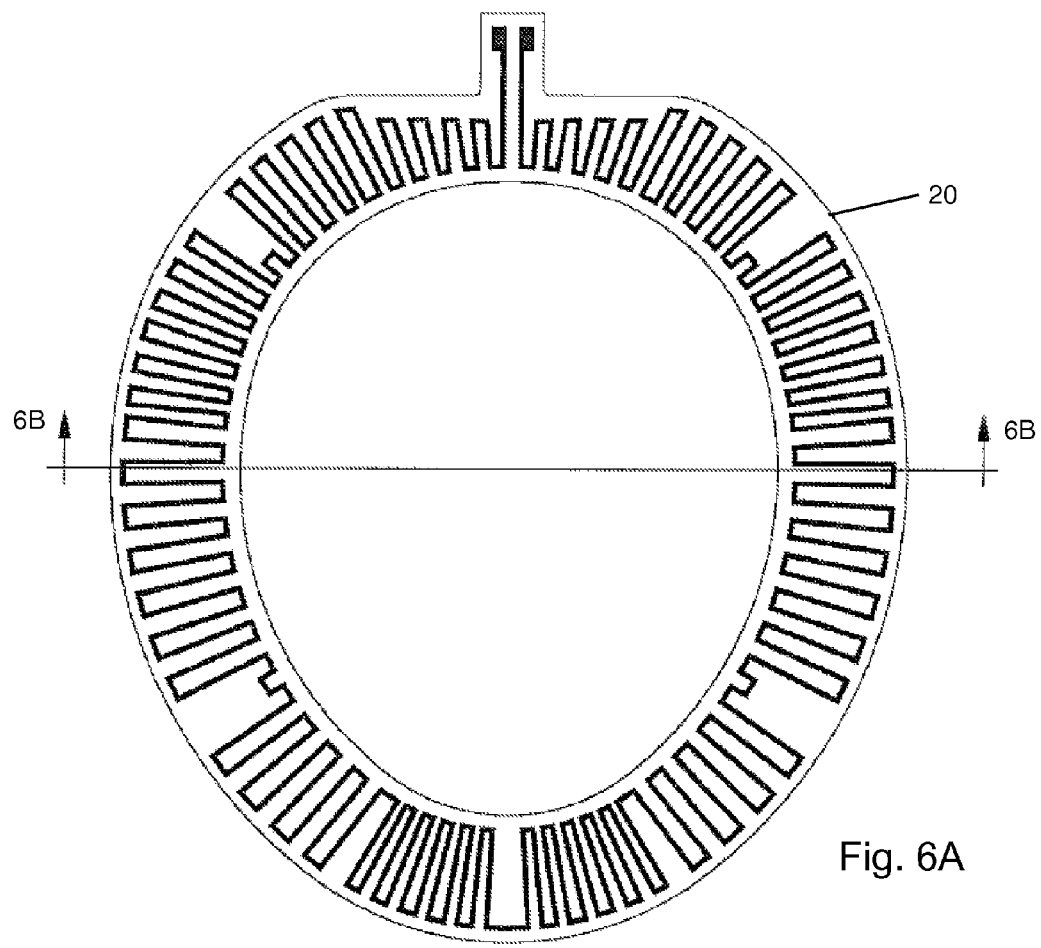
FIG. 6A shows a photochemically etched heater element made from metallised fabric and designed to be compression moulded as part of a shaped component, such as a toilet seat.
Figure 6B:
FIG. 6B is a cross-sectional view through the line 6B-6B of FIG. 6A.

Next, the fabric is exposed to a suitable image pattern of ultraviolet light from the phototool. This image is developed. The unrequired metal is then progressively etched away. Then, the photoresist is removed to leave the required metallic track shape for the heater element 20, as shown in FIGS. 6A and 6B. These steps will be clear to the skilled person.

The heater element is formed with a flexible tail portion. The tail has conductive tracks formed in the same way as the remainder of the heater element. At the end of the tail are formed termination pads for electrical connection of the heater element to a suitable power supply and control circuitry.

A suitable power supply (not shown) is mains power, transformed to an appropriate voltage as necessary.

In a preferred embodiment, functional chemicals are incorporated into the toilet seat. These functional chemicals are for initiation by operation of the heater element. Suitable chemicals include antimicrobials (to suppress or kill microbiological activity), insect repellents (to repel mosquitoes etc.), fragrances and perfumes. In a preferred approach such chemicals are microencapsulated in microcapsules, which melt at a particular initiation temperature or others, which allow diffusion of the active chemicals through their walls to effect a slow release mechanism within the formed component.

By appropriate temperature control, the heater element in the formed component for example may be used to initiate the delivery of the active chemicals. It will be understood that by the encapsulation of various active chemicals and the use of microcapsules having different thermal characteristics, the timing of the delivery of each chemical can be controlled as required. Normally, the microencapsulated components will not form part of the heater element itself rather they will be contained within the component material, e.g. in layer 16 and/or layer 18. The release of the chemicals is however achieved using the heater.

For a specific example of a microencapsulated insect repellent, the microcapsules of US-A-20030124167 are applied to a surface layer of the formed component.

Suitable materials for encapsulating suitable agents include lipids such as wax, paraffin, tristearin, stearic acid, monoglycerides, diglycerides, beeswax, oils, fats and hardened oils.

Suitable perfumes and fragrances are known. These may be encapsulated in wax, for example.

Suitable microencapsulated fragrances are available from Celessence International, of Hatch End, Pinner, Middlesex, HA5 4AB, UK.

In a further preferred embodiment, one or more high resolution digital images are applied to the formed component (in this case, a toilet seat). This can improve the aesthetic design and appearance for the purpose of personalisation. Suitable methods for application of such digital images include Thermostatic Printing (Registered Trade Mark) or dye sublimation if the component is composed of a compatible polymer (e.g. polyester PBT) or has a suitable polymer coating (e.g. acrylic, polyester, polyurethane etc.). Alternatively, the product may be ink jet printed directly for the purpose of decoration. These high resolution digital imaging printing processes do not interfere with the performance of the formed component with or without a heater element.

The embodiments above have been described by way of example. Modifications of these embodiments, further embodiments and modifications thereof will be apparent to the skilled person on reading this disclosure and as such are within the scope of the invention.

The invention claimed is:

1. A method of manufacturing a shaped component, having an outer surface, comprising the steps of:
   providing a heater element; the heater element including a metallised substrate of porous fabric having a plurality of components each encapsulated in metal wherein the metal on the metallised substrate of porous fabric is photochemically etched by selectively etching out metal encapsulated about the plurality of components of the metallised substrate of porous fabric to create at least one electrical heat generating circuit with first portions of the porous fabric being encapsulated with metal and second portions of the porous fabric not being encapsulated with metal; heat being generated by the first portions of the porous fabric;
   moulding a formable material around and through the heater element to create a shaped component; the heater element being located within the shaped component.

2. A method according to claim 1 further including the step of:
   printing an image onto the outer surface of the shaped component.

3. A method of manufacturing a shaped component, having an outer surface, comprising the steps of:
   providing a heater element; the heater element including a metallised substrate of porous fabric having a plurality of components each encapsulated in metal wherein the metal on the metallised substrate of porous fabric is photochemically etched by selectively etching out metal encapsulated about the plurality of components of the metallised substrate of porous fabric to create at least one electrical heat generating circuit with first portions of the porous fabric being encapsulated with metal and second portions of the porous fabric not being encapsulated with metal; heat being generated by the first portions of the porous fabric;
   moulding a formable material around and through the heater element to create a shaped component; the heater element being located within said the shaped component;
   the shaped component containing functional chemicals contained in microcapsules for delivery to the environment.

4. The method of claim 3, further comprising the step of:
   controlling heat output of the heater element by a thermal regulation device.

5. A method according to claim 3, further comprising the step of:
   printing an image onto the outer surface of the shaped component.

6. A method according to claim 3, further comprising the steps of:
   providing more than one type of functional chemical agent contained in different types of microcapsules, having different thermal characteristics, within the shaped component;

timing the delivery of each of the more than one type of functional chemical according to a predetermined schedule due to the thermal characteristics of the microcapsules.

7. A method according to claim 3, further comprising the steps of:
   providing more than one type of functional chemical contained in the same type of microcapsule within the shaped component;
   timing the delivery of each of the more than one type of functional chemical according to a predetermined schedule due to the thermal characteristics of the microcapsules.

8. A method according to claim 3, further comprising the steps of:
   providing at least one type of functional chemical within the shaped component;
   timing the delivery of the at least one type of functional chemical according to a predetermined schedule.

\* \* \* \* \*